United States Patent [19]

Mayr et al.

[11] Patent Number: 5,024,945
[45] Date of Patent: Jun. 18, 1991

[54] PROCESS FOR OBTAINING SARCOSINE OXIDASE FROM MICROORGANISMS

[75] Inventors: Ulrich Mayr, Rosenheim; Helmgard Gauhl; Hans Seidel, both of Tutzing, all of Fed. Rep. of Germany

[73] Assignee: Boehringer Mannheim GmbH, Mannheim-Waldorf, Fed. Rep. of Germany

[21] Appl. No.: 629,504

[22] Filed: Jul. 10, 1984

[30] Foreign Application Priority Data

Jul. 26, 1983 [DE] Fed. Rep. of Germany ....... 3326888

[51] Int. Cl.$^5$ .......................... C12N 9/06; C12P 13/04
[52] U.S. Cl. ..................... 435/191; 435/106; 435/874
[58] Field of Search ................ 435/191, 815, 874, 106

[56] References Cited

U.S. PATENT DOCUMENTS 3,794,562  2/1974  Bergmeyer et al. ................ 435/190
4,216,292  8/1980  Ikuta et al. ........................... 435/191
4,461,833  7/1984  Gordon ................................ 435/815

OTHER PUBLICATIONS

Frisell, Archives Biochemistry and Biophysics, vol. 142, pp. 213–222 (1971).
Microbial Enzymes and Bioconversions, ed. by Rose, vol. 5, pp. 142, 143 (1980).
Agric. Biol. Chem. 43 (6), 1197–1203, 1979.
Biochemical and Biophysical Research Communications, vol. 46, No. 2, 1972, pp. 885–891.
Chemical Abstracts, vol. 74, No. 19, Apr. 1971, No. 95794b.

Primary Examiner—David M. Naff
Assistant Examiner—Charles L. Patterson, Jr.

[57] ABSTRACT

The present invention provides a process for obtaining sarcosine oxidase from micro-organisms by culturing thereof and obtaining the enzyme from the biomass or from the culture broth, wherein a Pseudomonas strain is cultured.

8 Claims, No Drawings

PROCESS FOR OBTAINING SARCOSINE OXIDASE FROM MICROORGANISMS

The present invention is concerned with a process for obtaining sarcosine oxidase from micro-organisms.

Sarcosine oxidase (E.C. 1.5.3.1) is known and has already been obtained from micro-organisms, such as Corynebacteria, Arthrobacter, Bacillus and Cylindrocarbon. The enzyme is technically of interest for the determination of sarcosine and of compounds which can be converted into sarcosine. It catalyses the reaction:

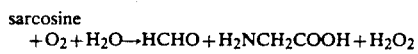

$$\text{sarcosine} + O_2 + H_2O \rightarrow HCHO + H_2NCH_2COOH + H_2O_2$$

The reaction products, especially hydrogen peroxide, can easily be determined by known methods.

The use of sarcosine oxidase in such a determination process is limited because it is laborious to obtain it from micro-organisms since all micro-organisms in which the enzyme has hitherto been found in amounts making working up thereof worthwhile are to be regarded as being relatively demanding, especially with regard to their culturability.

Therefore, it is an object of the present invention to provide a process for obtaining sarcosine oxidase from readily cultivatable, non-demanding, ubiquitous micro-organisms.

Thus, according to the present invention, there is provided a process for obtaining sarcosine oxidase from micro-organisms and obtaining the enzyme from the biomass or from the culture broth, wherein a Pseudomonas strain is cultured.

It is surprising that Pseudomonas contains sarcosine oxidase since hitherto only the presence of sarcosine dehydrogenase (E.C. 1.5.99.1) in this micro-organism was known (Agric. Biol. Chem., 43, 1197–1203/1979). Therefore, it was not to have been expected that a sarcosine oxidase was to be found in these micro-organisms, which are characterised by the above-mentioned properties of being easily cultivatable, non-demanding and widely occurring.

An especial advantage of the present invention is the fact that very high activities of sarcosine oxidase can be achieved and it was possible to find strains in which up to 20% of their soluble protein consisted of sarcosine oxidase (Sar-OD). Within the scope of the present invention, it is preferable to use the following Pseudomonas strains: *Pseudomonas maltophilia* (BMTU 254) DSM 2700 and *Pseudomonas maltophilia* (BMTU 288) DSM 2701.

The Pseudomonas strains used according to the present invention can be cultured extremely simply on a medium containing creatine or sarcosine as a source of carbon and nitrogen, as well as salts and trace elements.

An appropriate minimal culture medium consists, for example, of creatine or sarcosine, magnesium sulphate, sodium chloride, ammonium chloride, monopotassium dihydrogen phosphate and disodium monohydrogen phosphate. It is especially suitable for the selection of especially Sar-OD-rich strains. An appropriate solution of trace elements contains manganese, iron, calcium, copper, zinc, molybdenum and cobalt. For the production of Sar-OD, the micro-organisms are preferably allowed to grow on a medium which, besides creatine or sarcosine, also contains yeast extract, tryptone and sodium chloride.

Especially high yields can be achieved when the micro-organisms are incubated with nitrosoguanidine and the mutants thus obtained are subsequently further cultured on the above-mentioned minimal culture medium, the especially well-growing colonies thereby being isolated and further cultured.

The enzyme obtainable according to the process of the present invention has the following properties: pH optimum 8.0; temperature stability: 10 minutes at 37° C., pH 8.0, 84% residual activity; 10 minutes at 45° C. 13% residual activity; KM sarcosine, pH 8.0; 0.1M tris buffer, 25° C.; PAP detection system: $1.2 \times 10^{-2}$M.

The enzyme can be isolated according to the usual methods of enzyme purification, for example as described in Biochem. Biophys. Res. Comm., 96, 924–930/1980. However, there is preferred an enrichment process in which, after digestion, for example by high pressure dispersion, a polyethyleneimine fractionation is carried out and the active fraction obtained is chromatographed over hydrophobic Phenyl-Sepharose. Subsequently, there follows a molecular sieve fractionation and a high purification on Octyl-Sepharose. According to this process, a preparation with a specific activity of from 8 to 9 U/mg. can be obtained in a yield of over 30%.

After harvesting, the micro-organisms are preferably digested mechanically in a buffer solution of pH 6 to 9.5 which contains 0.1 to 0.3% by weight of polyethyleneimine. Insoluble material is separated off and the digest supernatant thus obtained is diluted with water or buffer solution to a polyethyleneimine content of 0.05% by weight, the Sar-OD thereby precipitating out and being obtained as a precipitate.

For the high purification of the enzyme preparation thus obtained, the preparation is preferably again taken up in buffer solution, fractionated over hydrophobic Phenyl-Sepharose, preferably with a decreasing gradient, the active fraction is fractionated with ammonium sulphate and the fraction precipitated out between 1.8 and 2.3M ammonium sulphate is subjected to a molecular sieve passage, for example on cross-linked agarose, and finally chromatographed over Octyl-Sepharose. There is thus obtained the pure enzyme which has a specific activity of about 8.4 U/mg.

For the use of the enzyme for analytical purposes, the high purification is not necessary or is not necessary to the full extent. If the crude enzyme obtained with polyethyleneimine still contains too many side activities for the determination, as a rule, in order to achieve a sufficient purity, it suffices to fractionate it over Phenyl-Sepharose and with ammonium sulphate.

The enzyme obtainable by the process according to the present invention corresponds in its properties to the known enzyme and, therefore, does not here require to be described in more detail. By means of the process according to the present invention, the enzyme can be obtained in a simple manner and in high yields and can, for example, be used for the determination of sarcosine or of substances which can be converted into sarcosine, such as creatinine, in biological fluids.

The following Examples are given for the purpose of illustrating the present invention:

EXAMPLE 1

The Pseudomonas strain was fermented at 30° C. for about 20 hours in a minimal medium of the following composition: per liter:
7.0 g. disodium monohydrogen phosphate dihydrate
3.0 g. monopotassium dihydrogen phosphate
1.0 g. ammonium chloride
0.05 g. sodium chloride
5 ml. magnesium heptahydrate 10% (added after sterilisation)
1 ml. trace solution+

+the trace solution contains, per 100 ml., 0.1 g. manganese sulphate dihydrate; 0.1 g. ferrous sulphate heptahydrate; 0.1 g. calcium chloride dihydrate; 0.01 g. copper sulphate pentahydrate; 0.01 g. zinc chloride; 0.01 g. ammonium molybdate; and 0.01 g. cobalt sulphate heptahydrate.

10 g. creatine or sarcosine (separately sterilised)
pH 7

The following Sar-OD activities were thereby measured by determination of the hydrogen peroxide formed:

|  | BMTU No. | corresp. DSM No. | Sar-OD activity, U/litre culture broth |
|---|---|---|---|
| Pseudomonas maltophilia | 254 | 2700 | 30 |
| Pseudomonas maltophilia | 288 | 2701 | 25 |

EXAMPLE 2

Pseudomonas maltophilia (BMTU 254) DSM 2700 was cultured aerobically in LB medium (1% Difco, 0.5% Difco yeast extract, 0.5% sodium chloride; pH 7.2) at 28° C. up to an OD of 400 to 600 nm=1. The cells were washed with 0.1M citrate buffer (pH 5.5), incubated in the same buffer with nitrosoguanidine (80 $\mu$g/ml.) for 60 minutes at 30° C. and thereafter washed with 0.1 M phosphate buffer (pH 7.0). Subsequently, there followed an aerobic culturing for 3 hours in LB medium at 28° C. The cells were again washed with the above phosphate buffer and plated out on minimal medium (0.6% disodium monohydrogen phosphate, 0.3% monopotassium dihydrogen phosphate, 0.05% sodium chloride, 1 mM magnesium sulphate, 0.1 mM calcium chloride and 1 ml. trace solution per liter of medium) (the trace solution contains, per 100 ml., 0.007 g. ferrous sulphate heptahydrate, 0.015 g. manganese chloride tetrahydrate, 0.015 g. zinc sulphate heptahydrate, 0.0015 g. copper sulphate pentahydrate, 0.0015 g. calcium chloride hexahydrate, 0.0015 g. sodium molybdate dihydrate and 0.0015 g. nickel chloride hexahydrate) with 0.5% creatine or sarcosine as a source of carbon and nitrogen. The mutants which grow better than the initial strain were isolated and, according to the above-described principle, subjected to a further nitrosoguanidine treatment and a subsequent selection on minimal medium with 0.5% creatine or sacrosine.

The isolate obtained from this selection was fermented in a medium of the following composition for about 32 hours:
1% Difco tryptone
0.5% Difco yeast extract
0.5% sarcosine
0.5% sodium chloride
pH 7.1; 25° C.

An activity yield of 1200 U/liter of culture solution was achieved. In the crude extract supernatant, there was measured a specific activity of the sarcosine oxidase of 1.9 U/mg. This corresponds to about 22% of the soluble protein.

EXAMPLE 3

Isolation of sarcosine oxidase (E.C. 1.5.3.1)

2.1 kg. of a moist mass of Pseudomonas maltochilia (BMTU 254, DSM 2700) (obtained from 100 liters of culture solution; Example 2) were suspended in 200 mmol/liter tris buffer (pH 8.0) (18 liters) and extracted 4 times at 650 ats. in a high pressure dispersion machine. So much Polimin $G_{35}$ (BASF) was added to the digest solution that a substantial separation of nucleic acid and foreign proteins took place (0.2%). For the positive precipitation of the enzyme, it suffices to dilute with water. The sarcosine oxidase precipitate was dissolved with 1.5 liters of 20 mmol/liters tris containing 1 mmol/liter ammonium sulphate (pH 8.0) and dialysed. This was followed by a hydrophobic chromatography on Phenyl-Sepharose (pH 8.0) with a decreasing gradient. After a salt fractionation by means of ammonium sulphate between 1.8 and 2.3 mol/liter, there was carried out a molecular sieve passage in Sepharose $S_{200}$ (Pharmacia). The sarcosine oxidase peak was purified on Octyl-Sepharose between pH 6.3 and 7.0 (increasing pH gradient) up to 8.3 U/mg. The purified enzyme was free from uricase and catalase and, in the SDS disc electrophoresis, showed four different subunits like the enzyme from Corynebacterium species U96 of Suzuki (J. Biochem., 89, 599-607/1981). The following Table shows the enrichment and yields:

Sarcosine oxidase enrichment from 2.1 kg. moist mass of Pseudomonas maltophilia

| step | volume | units | protein | spec. act. | yield % |
|---|---|---|---|---|---|
| 4 × 650 ats | 18 l. | 1.4 × $10^5$ | 118 g. | 1.19 | 100 |
| Polimin $G_{35}$ fraction | 1.5 l. | 1.2 × $10^5$ | 53 g. | 2.26 | 85.7 |
| Phenyl-Sepharose | 765 ml. | 8.6 × $10^4$ | 16.5 g. | 5.2 | 61 |
| gel filtration $S_{200}$ | 260 ml. | 8.0 × $10^4$ | 11.4 g. | 7.0 | 57 |
| Octyl-Sepharose | 168 ml. | 6.65 × $10^4$ | 8.0 g. | 8.3 | 47.5 |

We claim:

1. Process for obtaining sarcosine oxidase which catalyzes the reaction between sarcosine and oxygen to form formaldehyde, glycine, and hydrogen peroxide, comprising:
   (i) culturing a Pseudomonas strain capable of producing said sarcosine oxidase under conditions favoring production thereof, and
   (ii) recovering said sarcosine oxidase.

2. Process of claim 1, further comprising mutating a wild type strain of Pseudomonas with nitrosoguanidine to form a mutant strain capable of increased production of said enzyme and culturing said mutant strain.

3. Process of claim 2, further comprising selecting said mutant strain by culturing on a medium containing creatine as a source of carbon and nitrogen.

4. Process of claim 1, comprising culturing said microorganism on a medium which contains tryptone, yeast extract, sodium chloride, trace elements, and at least one of creatine and sarcosine.

5. Process of claim 1, comprising recovering said enzyme by mechanically digesting said Pseudomonas in a buffer at a pH of from 6 to 9.5 which contains 0.1 to 0.3% by weight polyethyleneimine to form a supernatant and an insoluble portion, removing said insoluble portion, diluting said supernatant with water to yield a concentration of polyethyleneimine no greater than 0.05% with formation of a precipitate containing said enzyme and recovering said precipitate.

6. Process of claim 5, comprising purifying said precipitate containing sarcosine oxidase by dissolving said precipitate in a buffer, fractionating the dissolved precipitate over hydrophobic Phenyl-Sepharose to separate an active fraction, treating said active fraction with ammonium sulphate at a concentration of 1.8 to 2.3M to form an insoluble fraction, subjecting said insoluble fraction to molecular sieve fractionation, and chromatographing on Octyl-Sepharose to obtain said enzyme.

7. A process for obtaining sarocosine oxidase from micro-organisms comprising the steps of culturing a Pesudomonas strain selected from the group consisting of *Pseudomonas maltophilia* (BMTU 254) DSM 2700 and *Pseudomonas maltophilia* (BMTU 288) DSM 2701, and recovering the enzyme from the micro-organism biomass or from the culture broth.

8. The process of claim 7 further comprising treating the Pseudomonas strain with nitrosoguanidine to form mutants and selecting the mutants by using creatine as a source of carbon and nitrogen.

* * * * *